United States Patent [19]

Kantrowitz et al.

[11] Patent Number: 4,634,422

[45] Date of Patent: Jan. 6, 1987

[54] PERCUTANEOUS ACCESS DEVICE AND METHOD FOR IMPLANTING SAME

[76] Inventors: Adrian Kantrowitz, 70 Gallogly Rd., Pontiac, Mich. 48055; Paul S. Freed, 1486 Sodon Ct., Bloomfield Hills, Mich. 48013; Frizell L. Vaughan, 1336 Culver Rd., Ann Arbor, Mich. 48103; Isadore A. Bernstein, 1200 Arlington; Robert H. Gray, 2780 Carmel St., both of Ann Arbor, Mich. 48104

[21] Appl. No.: 615,883

[22] Filed: May 31, 1984

[51] Int. Cl.[4] .................... A61M 31/00; A61M 5/32; C12N 5/02

[52] U.S. Cl. ........................ 604/49; 604/175; 623/66; 435/241

[58] Field of Search .............. 604/175, 174, 49–51; 3/1.3, 1 A, 1 C, 1, 1.1, 36, 1.4; 435/240–241; 623/66

[56] References Cited

U.S. PATENT DOCUMENTS

| | | |
|---|---|---|
| 3,700,380 | 10/1972 | Kitrilakis ........................... 3/1 |
| 3,826,241 | 7/1974 | Bucalo .............................. 128/1 R |
| 3,906,549 | 9/1975 | Bucalo .............................. 128/1 R |
| 4,004,298 | 1/1977 | Freed ................................ 3/1 C |
| 4,154,652 | 5/1979 | Sawamura et al. | |
| 4,217,889 | 8/1980 | Radovan et al. ................... 128/1 R |
| 4,254,226 | 3/1981 | Elsinger et al. .................... 435/240 |

FOREIGN PATENT DOCUMENTS

WO82/03764 11/1982 PCT Int'l Appl. .................. 3/1

OTHER PUBLICATIONS

Molecular Biology of the Cell, Alberts et al., 1983, p. 693.

"Development of a Percutaneous Energy Transmission System" by Kantrowitz et al., May, 1982.

Primary Examiner—C. Fred Rosenbaum
Assistant Examiner—Gene B. Kartchner
Attorney, Agent, or Firm—Basile, Weintraub & Hanlon

[57] ABSTRACT

A percutaneous access device (PAD) is provided with a sleeve or separable member which may be detached from the device to enable the culturing of a multilayer fibroblast coating on the member in a stable and undisturbed environment. The member is constructed so that when it is assembled into the device and the device is implanted in a patient, the cultured coating of the member is exposed to the patient's dermis whose fibroblasts will, after a relatively short healing period, merge with the fibroblasts of the coating to form a barrier layer interlocked with the member to prevent epidermal ingrowth or marsupialization of the implanted device.

Implantation techniques for further facilitating the formation of the dermal barrier are also disclosed.

5 Claims, 7 Drawing Figures

PERCUTANEOUS ACCESS DEVICE AND METHOD FOR IMPLANTING SAME

BACKGROUND OF THE INVENTION

The invention described herein was made in the course of work under a grant or award from the Department of Health, Education and Welfare.

Percutaneous access devices, hereinafter referred to as PADs, are employed to establish a connection through the skin between an organ or device implanted within the human body and some external device. The present invention is especially concerned with PADs which are implanted on a long-term basis.

Although a substantial amount of research on devices of this type has been undertaken in recent years, the prior art in general has failed to adequately solve recurring problems of both mechanical and biological nature.

A basic problem confronted by such devices is that they must protrude through the skin, and the outer layer of skin or epidermis must necessarily be provided with an opening for such purpose. The epidermis has a natural propensity to attempt to close such unnatural openings and will attempt to externalize the embedded device by epidermal cell proliferation, resulting in marsupialization, or sinus-tract formation when marsupialization is not complete. Marsupialization tends to extrude the implanted device, while sinus-tract formation provides ideal conditions for the development of infection. Likelihood of infection can also occur upon displacement of the PAD relative to the skin which tears or ruptures the bond between the skin and protruding portion of the PAD.

It has been pointed out by Winter (see Transcutaneous Implants: Reactions of the Skin Implant Interface—J.Biomed.Mater.Res Symposium 5:99, 1974) that basal cells of the epidermis do not invade the underlying dermis layer under normal conditions and are probably prevented from doing so by collagen fibers in the dermis. This suggested the possibility of blocking down-growth of the epidermis along the side of the implanted device if the dermis could in some manner be firmly bonded or interlocked to the device to form a barrier.

The present invention is especially directed to methods and apparatus for forming such a barrier.

SUMMARY OF THE INVENTION

In accordance with the present invention, the PAD is constructed to include a member or element, usually in the form of a sleeve, which is separable from the device and which, when assembled into the device, forms the external surface of the device which is exposed to the dermis when the assembled device is implanted in the patient. The exposed surface of this member, which is constructed of a suitable biomedical material, is indented by a multiplicity of individual cavities into which portions of the dermal cells can grow or expand to mechanically interlock the dermis to the surface of the member to provide the desired barrier.

These cavities are formed by nuclear bombardment followed by an etching process and are of a size and spacing such that a single cell of the dermis will overlie at least two or more such cavities at any random location on the surface. The surface is referred to as a nanoporous surface.

The nanoporous surface of the member is precoated, prior to implantation, with a cultured coating of dermis prepared from dermis obtained from the patient.

Forming the cavities and applying the dermal precoating to an element or member which is separable from the PAD provides substantial convenience and efficiency by enabling these two procedures to be performed only on the member itself. It also achieves the major advantage of enabling the formation of the bond between the dermal precoating and the surface of the member to proceed in a more stable environment in which growth stimulating solutions can be effectively employed. It is a practical impossibility to prevent movement of the skin relative to the implanted device over the period of time required for the cells of the dermis to grow into the cavities in the member; hence, the formation of the bond between the device and precoat layers can proceed much more efficiently in a test tube.

Two implantation techniques have been developed. In the first, and preferred, technique, a dummy device of a shape similar to that of the device to be implanted is implanted entirely beneath the patient's skin just underneath the dermis. The incision through which the dummy device is inserted is then temporarily closed and the dummy device remains implanted for a first healing period of approximately two weeks. The healing process results in the formation of a clean pocket beneath the skin from which fluids and debris produced by the original insertion have been absorbed by the conclusion of the first healing period.

The original incision is then reopened, the dummy device removed and the PAD is inserted into the pocket formed by the dummy device. The incision is then closed, leaving the implanted PAD completely covered by skin. In accordance with the preferred method, the PAD is allowed to remain covered in place for a second healing period to allow the dermis of the patient to become firmly bonded to the precoated dermal layer on the nanoporous member, this member having been assembled to the PAD prior to its implantation. At the conclusion of this second healing period, the skin is excised above that portion of the PAD which is to project.

Under an alternative method, the excision of the epidermis above the projecting portion of the PAD is accomplished at the time the PAD is first implanted. This latter procedure is followed in those cases where there may be some urgency in placing the PAD in operation.

IN THE DRAWINGS

Figure 1:
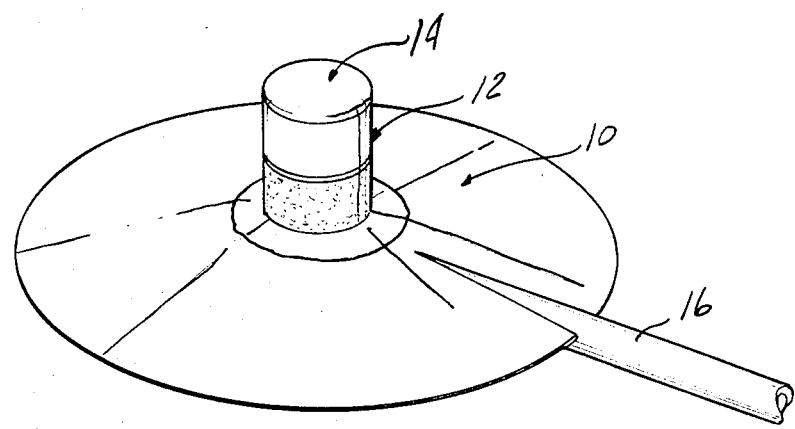
FIG. 1 is a perspective view of a PAD embodying the present invention.

For purposes of illustration, a PAD of the same general type as that disclosed in Freed U.S. Pat. No. 4,004,298 is shown in the drawings. This general type of PAD may be employed, for example, to supply a pneumatic connection and electrocardiogram lead connections to a dynamic aortic path of the type disclosed in Kantrowitz et al. U.S. Pat. No. 4,051,840. It will be understood, however, that the present invention is applicable to other forms of precutaneous devices.

Figure 2:
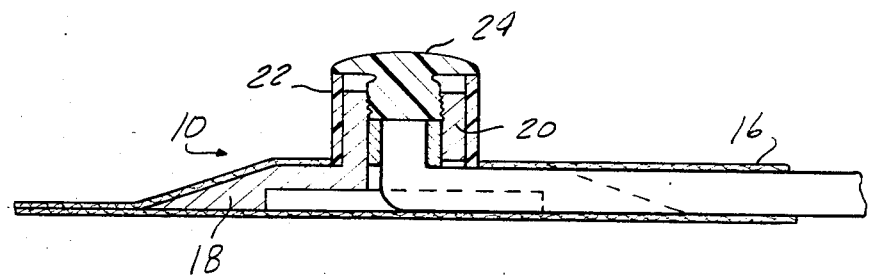
FIG. 2 is a cross-sectional view of the device of FIG. 1.

Referring first to FIG. 1, the PAD disclosed includes a main or base section designated generally 10, an extension 12 which, in FIG. 1, is closed by a cap 14 and a conduit 16. As best seen in FIG. 2, conduit 16 is mounted in a housing which includes a generally flat disk-shaped flange portion 18 and an integral, upwardly projecting neck 20 having a central passage into which one end of conduit 16 opens. Conduit 16 is fixedly secured to the housing in the position shown and the exposed surfaces of the flange 18 of the housing and conduit 16 are covered with a layer of an inert fibrous material, typically a commercially available, medically approved Dacron velour which provides a textured, fibrous surface into which body tissues can grow and interlock.

Referring particularly to FIG. 2, a hollow tubular sleeve 22 is shown closely surrounding the neck portion 20 of the housing. Sleeve 22 is formed of a suitable biomedical material, such as a polycarbonate material sold by the General Electric Company under the trademark Lexan 104, for example, whose exterior surface is formed with a multiplicity of tiny cavities, this surface being subsequently referred to as a nanoporous surface. The nanoporous surface is formed by a nuclear bombardment procedure in which the surface of sleeve 22 is exposed within a vacuum chamber to a Californium 252 spontaneous fission source and subsequently etched with an etching solution of 6.25 N NaOH etching solution at temperatures from between 45° C. to approximately 70° C. Etching temperatures near the lower end of the range produce cavities which are relatively deep as compared to their diameter, a desired feature. In a preferred embodiment, the cavities so formed will be distributed over the sleeve surface in a density of 15,000 or more cavities per square millimeter; the individual cavities will have diameters of the order of 0.5 to 1.0 micron and depths of 3 or more times their diameter. A fibroblast of the dermis typically has a size of 10 microns; hence, such a cell placed at any random location on the nanoporous surface of sleeve 22 would overlie two or more individual cavities.

Figure 3:
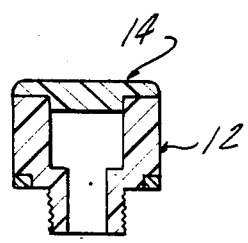
FIG. 3 is a cross-sectional view taken on a central vertical plane of an extension portion of the device of FIG. 1.

Sleeve 22 is not permanently assembled into the PAD until just prior to the time at which the PAD is implanted in the patient. A temporary cap 24 is provided for use during the implanting procedure.

Where the implanting technique to be described below is employed, it is desired to keep the height of the PAD as shown in FIG. 2 to a minimum because in this particular implanting procedure the device as shown in FIG. 2 may remain entirely beneath the patient's skin for approximately two weeks and upward pressure of the top of the neck portion of the implanted device against the skin may constrict the flow of blood through the skin. In this case, the extension section 12 of the complete PAD (FIG. 1) is made separable. The extension 12 is partially shown in FIG. 3 and will normally include the couplings or connections by means of which fluid conducting tubes or electric wires passing through control conduit 16 may be connected to external devices.

PRECOATING OF NANOPOROUS SURFACE

The purpose of the nanoporous surface of sleeve 22 is to provide a multiplicity of tiny cavities into which cells of the dermis can grow to firmly interlock the dermis to the exterior surface of the sleeve. This interlocking forms a barrier to downward growth of the epidermis, thereby preventing marsupialization of the implanted device and minimizing sinus tract formation.

Because the interlocking between the dermis and sleeve 22 is of a mechanical nature and dependent upon the growth of cells of the dermis into the cavities of the nanoporous surface, a certain amount of time is required before a bond of any meaningful integrity is achieved. On the other hand, portions of the dermis separated from each other, as by a minor cut, will rejoin and heal—i.e., bond—to each other in a matter of a few days. Because movement or stretching of the skin of a patient cannot be prevented over any reasonable period of time, the present invention utilizes what will be referred to as a precoating of the nanoporous sleeve surface with a multicell layer of dermal fibroblasts and collagen prior to implantation. In essence, under this technique a dermis-to-sleeve bond is formed prior to implantation and a dermis-to-dermis bond is formed after implantation.

To precoat the nanoporous surface of the sleeve, dermal tissue is obtained from the patient by biopsy and minced into pieces approximately 2 to 4 millimeters square. These pieces are then placed in a flask containing about one percent collagenase or tripsin dissolved in phosphate buffered saline and refrigerated overnight at 4° C. to 6° C. After 12 to 20 hours, the flask contents are stirred magnetically at room temperature for about one hour. The resulting suspension is decanted in a tube and centrifuged at 650 RPM for 5 minutes. The supernatant is discarded and the residue is resuspended in a complete medium by stirring to separate the suspended individual cells from remaining tissue fragments. The complete medium is made up of a commercially available medium sold under the name Eagle's Minimum Essential Medium supplemented with 10 percent fatal bovine serum, suitable growth additives and insulin and hydrocortisone, both 10 micrograms/ml, penicillin and streptomycin, both 100 micrograms/ml, and fungizone 0.05 micrograms/ml. The cell suspension is then seeded into a culture flask containing complete medium which is placed in an incubator.

The tissue fragments are stirred in complete medium for three or more hours to produce a further suspension of cells which is again removed and transferred to a culture flask for incubation. The steps of stirring to create a cell suspension and removing the cell suspension from the remaining tissue fragments to be incubated is repeated several times.

The culture containing the cell suspension in complete medium are all incubated at about 35° C. in a humidified atmosphere of 5 percent carbon dioxide and 95 percent air for about 10 days.

The resulting fibroblasts are then suspended in fresh complete medium to which ascorbic acid has been added and to sleeve within the nanoporous surface is immersed in this suspension. The suspension is then incubated with daily additions of fresh ascorbic acid for about 10 days.

In some cases, it may be desired to anchor or partially embed a percutaneous access device in bone. In this event, a coating of osteoblast on a nanoporous surface may be cultured by the foregoing procedure from small bone chips or scrapings obtained from the patient.

IMPLANTATION PROCEDURE

Implantation of the PAD necessarily requires the forming of an incision in the patient's skin and, in the case of a PAD of the type shown in the drawing, surgical formation of a pocket just underneath the dermis to receive the flange-like base of the particular type of PAD shown in the drawings. Regardless of the care with which such a pocket beneath the dermis is formed, the freshly formed pocket will contain substantial amounts of microscopic debris, such as blood clots, coagulum, microscopic pieces of fat, cotton filaments from gauze used to dry the field, etc. Such debris is of substantial size compared to the size of a dermal cell, and trapping of such debris between the surface of the PAD and the dermal layer upon insertion of the PAD can prevent or at least substantially interfere with the merging of the fibroblast in the skin and the fibroblast coating on the sleeve.

To circumvent this problem, instead of implanting the PAD in the freshly formed pocket beneath the dermal layer, a dummy device (template) of a material, such as silicone rubber, having a shape substantially the same as that of the PAD, is inserted into the freshly formed pocket and the incision is then temporarily closed. The dummy device is implanted for a period of two weeks or so, this period of implantation occurring during the time in which the fibroblast collagen layer is being cultured and grown on the nanoporous surface of the sleeve.

This two-week healing period enables the host tissues to resorb or encapsulate the debris from the pocket so that upon removal of the dummy device and insertion of the PAD into the pocket, the fibroblasts of the host and sleeve can achieve full face-to-face contact with each other.

Figure 4:
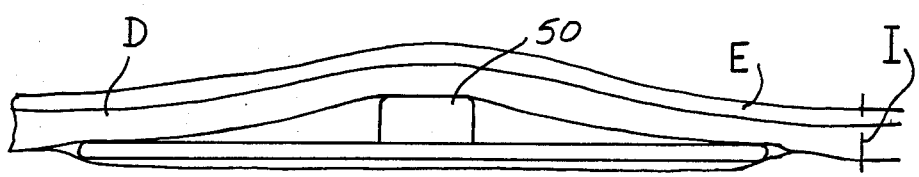
FIG. 4 is a cross-sectional view illustrating an initial step in the implanting of a device.
Figure 5:
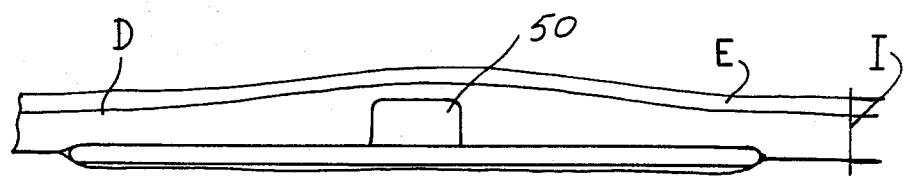
FIGS. 5, 6 and 7 are views similar to FIG. 4 illustrating subsequent steps in the implanting process.

In FIGS. 4 and 5, a dummy device 50 is shown implanted beneath the patient's skin. FIG. 4 shows the device as it is initially implanted. It will be noted that the incision I through which the device is inserted is located to one side of the pocket and the dummy device 50 thus, when inserted, is completely covered by unbroken layers of dermis D and epidermis E.

With a PAD of the configuration shown in the drawings, the upwardly projecting central portion of dummy device 50 representing the neck of the PAD will exert an upward pressure against the overlying layers of dermis and epidermis, thus tending to apply pressure against tiny blood vessels or capillaries in the portions of the skin overlying the upwardly projecting portion. To minimize this pressure, the height of the upwardly projecting central portion above the flange portion of device 50 is preferably limited to 7 mm.

In FIG. 5, the dummy device 50 is shown near the end of the healing period, and it will be observed that at this time the dermis has grown to closely conform itself to the upwardly projecting central portion or neck of the dummy device.

The implantation may be accomplished by either of what will be referred to as a two-step process or a three-step process. In both processes, the first step is the temporary implantation of dummy device 50 as described above.

In the two-step process, the precoated sleeve 22 is carefully assembled upon the PAD just prior to implantation and, in most cases where the completed PAD includes a separate extension section 12, the extension may be assembled upon the PAD prior to implantation.

Upon removal of dummy device 50, the PAD is inserted into the pocket, and the dermis and epidermis overlying the upper end of the implanted PAD is excised to allow the neck of the implanted PAD to project through the skin.

Figure 7:
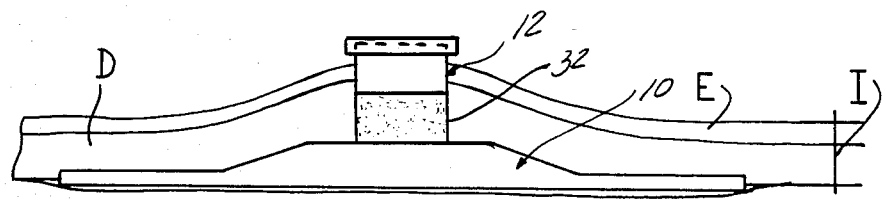

When this procedure is followed (FIG. 7), efforts are made to remove as much debris and fluids resulting from the excision to the exterior of the skin.

In those cases where time permits, the three-step process is preferred. In the three-step process, after assembly of the coated sleeve upon the PAD, the PAD is capped as shown in FIG. 2 and inserted into the pocket in place of the dummy device and the incision I is reclosed. When so capped, as in FIG. 2, the upward projection of the sleeve and neck above the horizontal flange portion of the PAD is of relatively short height, again preferably no greater than 7 mm.

Figure 6:
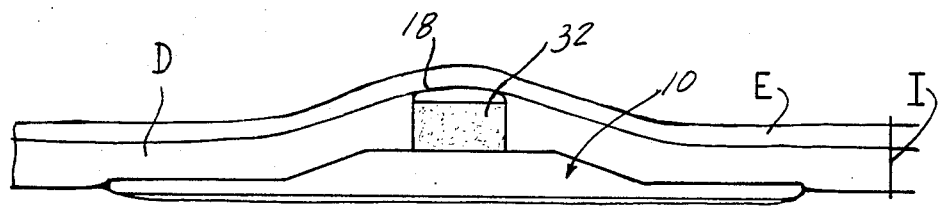

In the three-step process, the PAD in the configuration of FIG. 2 is allowed to remain in place, completely covered by an unbroken layer of dermis and epidermis (FIG. 6) for a healing period nominally of two weeks. During this latter healing period, the fibroblasts of the dermis of the patient have the opportunity to become firmly merged with the fibroblast coating of sleeve 22, while the fibroblasts of the coating of the sleeve have a further opportunity to grow into and more firmly interlock with the pores or cavities in the nanoporous surface of sleeve 22. Thus, a firm interlock between the dermis of the patient and sleeve 22 is formed before the dermis and epidermis adjacent this region is excised. Upon excision of the dermis and epidermis overlying cap 24, the cap 24 is removed and replaced by extension 12. As employed in the following claims, the term "nanoporous surface" is to be construed as a surface having multiplicity of microscopic cavities or pores of diameters of approximately 0.5 to 1.0 microns and depths of three or more times their diameter distributed over the surface in a density of 15,000 or more cavities per square millimeter.

While specific structures and methods for implanting a PAD have been described, it will be apparent to those skilled in the art that the structures and methods may be modified. Therefore, the foregoing description is to be considered exemplary rather than limiting, and the true scope of the invention is that defined in the following claims.

We claim:

1. In a percutaneous device adapted to be implanted beneath the skin of a patient and to project outwardly through the skin; the improvement comprising a detachable member adapted to be assembled to said device at a location such that the external surface of said member constitutes the surface of said device which passes through and is exposed to the dermis of the patient when the device is implanted, means defining a multiplicity of pores or cavities in said external surface of diameters and distribution such that a dermal cell placed at random on said external surface will overlie at least two of said pores or cavities, said pores or cavities having diameters between about 0.5 and about 1.0 microns and depths of at least three times their respective diameters.

2. The invention as defined in claim 1 wherein said external surface is covered with a cultured autologous miltilayer fibroblast coating prior to being assembled upon said device.

3. The method of implanting a percutaneous device beneath the skin of a patient with a portion of the device projecting outwardly through the skin wherein that portion of the surface of the device which, when implanted, is exposed to the dermis is constituted by a nanoporous surface on a member detachable from the device, said method comprising the steps of:

A. surgically forming a pocket beneath the dermis of a patient,
B. inserting into said pocket a dummy device having a shape substantially similar to that of that portion of the percutaneous device which, when the percutaneous device is implanted, will lie beneath the epidermis of the patient,
C. allowing said dummy device to remain undisturbed in said pocket for a period of time sufficient to allow resorption of surgical debris resulting from the formation of the pocket,
D. removing the dummy device from said pocket and inserting the percutaneous device with the detachable member assembled thereto into said pocket after the detachable member has been cultured with a multilayer fibroblast coating on the nanoporous surface and attached to the access device prior to insertion into the pocket.

4. The method defined in claim 3 comprising the further steps of allowing said percutaneous device to remain undisturbed in said pocket for a period of time sufficient to permit integration of the fibroblast coating on said member with the dermis of the patient before excising the epidermis to provide extracorporeal access to said device.

5. The method of applying a multilayer fibroblast coating upon a nanoporous surface comprising the steps of:

A. placing a quantity of finely minced dermal tissue in a tripsin or collagenase solution and refrigerating said solution for about 18 hours,
B. removing the enzyme solution and resuspending the minced tissue in a complete medium comprising Eagle's minimum essential medium supplemented with fetal bovine serum plus growth additives,
C. stirring the mixture at room temperature for one hour and removing the resulting cell suspension from the tissue and sedimenting said suspension,
D. resuspending the sediment in the aforementioned complete medium and seeding the resulting suspension in the cultured flask,
E. adding more complete medium to the remaining tissue and stirring the mixture for three or more hours,
F. removing the resulting cell suspension from the tissue and sedimenting said suspension,
G. resuspending the sediment in the aforementioned complete medium and seeding the resulting suspension in a cultured flask,
H. repeating steps F and G to obtain the cell suspension for seeding a third cultured flask,
I. incubating the seeded flask at 35° C. in a humidified atmosphere of 5 percent carbon dioxide and 95 percent air for 10 days,
J. harvesting the resulting fibroblasts by suspending them in fresh complete medium with ascorbic acid added, and
K. immersing the nanoporous surface to be coated in the suspension described in Step J contained in a culture well and incubating said culture with daily addition of fresh ascorbic acid for a period sufficient to bond a multilayer coating to the said surface.

* * * * *